Figure 1:
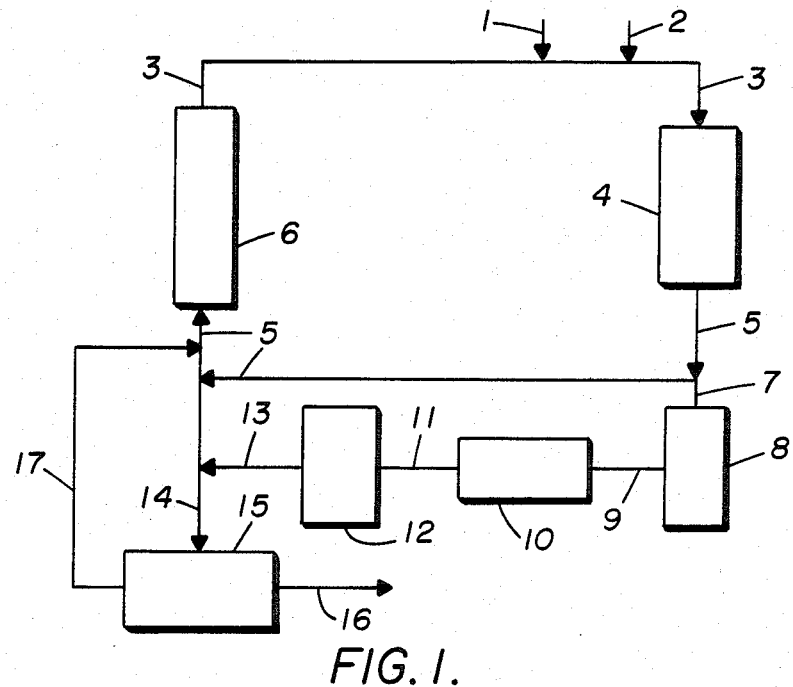

United States Patent [19]

Coleman et al.

[11] Patent Number: 4,526,990

[45] Date of Patent: Jul. 2, 1985

[54] SYNTHESIS OF γ-VINYL-γ-BUTYROLACTONE FROM ACETOXYHEXENOIC ACIDS

[75] Inventors: James P. Coleman; Richard C. Hallcher, both of Maryland Heights; Thomas E. Rogers, Manchester; Dudley E. McMackins, St. Charles, all of Mo.

[73] Assignee: Monsanto Company, St. Louis, Mo.

[21] Appl. No.: 503,979

[22] Filed: Jun. 13, 1983

[51] Int. Cl.$^3$ .................... C07D 307/32; C07C 67/05
[52] U.S. Cl. ..................................... 549/326; 560/241
[58] Field of Search ........................ 549/326; 560/241

[56] References Cited

U.S. PATENT DOCUMENTS 3,927,051 12/1975 de Klein .............................. 260/413
3,992,417 11/1976 Dessau et al. .................... 260/343.6
4,158,741 9/1979 Goi et al. ............................. 562/599
4,175,089 11/1979 Heiba et al. ....................... 260/343.6
4,356,317 10/1982 Colemen et al. ..................... 560/241
4,380,650 4/1983 Colemen et al. ..................... 549/326

FOREIGN PATENT DOCUMENTS 1219332 1/1971 United Kingdom .

Primary Examiner—Norma S. Milestone
Attorney, Agent, or Firm—Joseph D. Kennedy; James W. Williams, Jr.

[57] ABSTRACT

In the process of preparing acetoxyhexenoic acids from butadiene, acetic acid and acetic anhydride, selectivity is improved by converting the acetoxyhexenoic acids to γ-vinyl-γ-butyrolactone before isolation. Copper and platinum are useful catalysts in the conversion.

17 Claims, 5 Drawing Figures

SYNTHESIS OF γ-VINYL-γ-BUTYROLACTONE FROM ACETOXYHEXENOIC ACIDS

The present invention concerns a method of preparing acetoxyhexenoic acids and converting them in situ to γ-vinyl-γ-butyrolactone in order to improve selectivity to desired products and have a more readily isolable product.

The present invention further concerns a method of converting acyloxyhexenoic acids to γ-vinyl-γ-butyrolactone by heating such acids in the presence of cuprous ion or platinum black, and particularly when effected also in the presence of manganese and other components present in a reaction mixture in which acyloxy hexenoic acids are produced.

BACKGROUND OF THE INVENTION

A prior commonly assigned copending U.S. patent application of Coleman, Hallcher and McMackins, Ser. No. 222,200, filed Jan. 2, 1981 now U.S. Pat. No. 4,356,317, describes a procedure to react butadiene and acetic acid with metal ion oxidant to prepare acetoxyhexenoic acids which are then converted to sorbic acid. A. U.S. Pat. No. 4,175,089, describes a procedure for reacting olefins and acetic acid with metal ion oxidant to produce lactones. U.S. Pat. Nos. 4,022,822 and 4,158,741 have described procedures for converting γ-vinyl-γ-butyrolactone to sorbic acid. A prior commonly assigned U.S. patent application Ser. No. 222,199, of Coleman, Hallcher and McMackins, filed Jan. 2, 1981, now U.S. Pat. No. 4,380,650 describes a procedure for converting acetoxyhexenoic acids to γ-vinyl-γ-butyrolactone.

SUMMARY OF THE INVENTION

The present invention involves the reaction of butadiene, acetic acid and acetic anhydride with a metal ion oxidant to produce acetoxyhexenoic acids, followed by a step to convert the acetoxyhexenoic acids without separation from the reaction mixture, to γ-vinyl-γ-butyrolactone, and separation of the lactone from the reaction mixture. It is further advantageous and part of the invention to recycle lactone-containing reaction mixture back to the initial reaction zone for further reaction of the butadiene acetic acid and acetic acid reactants with the metal oxidant component to produce more acetoxyhexenoic acids. In a procedure in which the metal oxidant is regenerated in an electrolysis cell for recycle to the butadiene and acetic acid reaction, lactone containing reaction mixture may be recycled through the electrolysis cell to the reaction. In a particular aspect the invention involves the use of monovalent copper or platinum black as catalysis for the conversion of acetoxyhexenoic acids to γ-vinyl-γ-butyrolactone, particularly in the presence of manganese, and procedures for converting copper to the monovalent state and avoiding its oxidation to divalent copper, and for converting manganese to the divalent state. The cuprous ion or zero valent platinum are effective even in the presence of manganese or other components from a reaction mixture for producing acetoxyhexenoic acids from butadiene and acetic acid with trivalent manganese as an oxidant.

The conversion of the acetoxyhexenoic acids to the lactone, is useful in permitting greater efficiency in the process for producing the acetoxyhexenoic acids, and in providing a more readily separable product. The invention further involves procedures for converting copper to the mono-valent form for use in the process. And the use of such procedures in conjunction with procedures in which copper is used in the divalent state in the preparation of acetoxyhexenoic acids, and particularly in conjunction with procedures in which the divalent copper is regenerated electrolytically during the preparation of acetoxyhexenoic acids. In one particular aspect, the copper may be converted to cuprous form for use herein by reduction at the cathode of an electrolysis cell. While presently of most interest in conjunction with reactions involving manganese as a metal oxidant, the various aspects of the present invention can also be used in reactions involving other metal ion oxidants in reactions of butadiene, acetic acid and acetic anhydride to produce acetoxyhexenoic acids, particularly vanadium or cerium ions, which are effective oxidants as pentavalent vanadium and tetravalent cerium. As with manganese, appropriate valence states for the reaction can be obtained by oxidation as by electrolysis.

DETAILED DISCLOSURE

The present invention concerns a process for reacting butadiene and acetic acid to produce acetoxyhexenoic acids, which is useful as part of a multistep route to sorbic acid. The process can be conducted with good initial selectivity to the acetoxyhexenoic acids product, and is amenable to use as a continuous process with electrolytic regeneration of the metal ion oxidant employed. However, it has been found that the acetoxyacids product tends to be unstable in the reaction mixture and selectivity to such product tends to decline as conversions are increased, or as product concentrations in the reaction mixture are increased. It has further been found that γ-vinyl-γ-butyrolactone is less sensitive to competitive reactions. In addition, the lactone is more volatile than the acetoxyacids and appears amenable to easier separation and purification. The present invention involves the conversion of acetoxyacids to γ-vinyl-γ-butyrolactone in order to provide a more stable product, which can be obtained with good selectivity at higher conversions.

FIG. 1 is a flow sheet of a system for reaction of butadiene, acetic acid and acetic anhydride with metal salt oxidant to produce acetoxyhexenoic acids, and then to convert the acids to γ-vinyl-γ-butyrolactone.

As indicated hereinabove, procedures are known for reacting butadiene and acetic acid to produce γ-vinyl-γ-butyrolactone. However, it has been found that reactions leading directly or immediately to the lactone, utilizing conditions or agents to produce lactone from butadiene and acetic acid, are in general extremely slow by comparison to reactions producing acetoxyhexenoic acids. Also the reactions were often comparatively low in current efficiency and yield of product. Thus there is an advantage in conducting a comparatively efficient reaction to produce acetoxyhexenoic acids, and then converting to γ-vinyl-γ-butyrolactone prior to separation of product in order to lessen degradation of the product in the reaction mixture.

The referred to application Ser. No. 222,200 concerns a process in which butadiene and acetic acid are reacted in the presence of a metal salt oxidant, usually trivalent manganese, to produce acetoxyhexenoic acids. Vanadium or cerium can be substituted for the manganese there, and also in the present invention, but the preferred manganese will be used for exemplification herein. Acetic anhydride is also present with the effect of enhancing the reaction rate and selectivity of the process to acetoxyhexenoic acids. The acetoxyhexenoic acids produced are 6-acetoxy-4-hexenoic acid and 4-acetoxy-5-hexenoic acid. The process is conducted on a continuous basis with electrolytic regeneration of the trivalent manganese. The reaction stream can be cycled from a reactor through the anode chamber of a divided electrolysis cell to achieve such regeneration. Cupric ion is also preferably used in the process described in said application, and it too is regenerated electrolytically or by reaction with regenerated manganese III.

During a process for producing acetoxyhexenoic acids, the reaction mixture will contain acetic acid, acetic anhydride and manganese and copper ions. The manganese will generally be in the divalent or trivalent state, and the copper in the divalent or monovalent state. In a continuous process in which the reaction mixture is cycled through an anode chamber for oxidation of metal salts, a substantial amount of the manganese will be in trivalent state, and copper in divalent state, after the mixture has been subjected to such oxidation. For that part of the reaction mixture which has been permitted to react extensively, as in a reaction chamber immediately before being cycled to the anode chamber of an electrolysis cell, the supply of trivalent manganese and divalent copper may be nearly exhausted, as the metal ions are reduced in reactions oxidizing other components of the reaction mixture. The reaction mixture will also contain butadiene, but the amount may be relatively low after extensive reaction before recycle.

The reaction producing acetoxyhexenoic acids can be summarized:

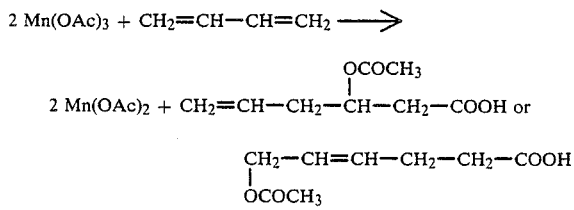

It is to be understood that acetic acid or acetic anhydride may take part in the reaction forming free radical or other intermediates, and that copper, when present is also involved in oxidation of intermediates.

It has been found that monovalent copper effectively catalyzes the conversion of acetoxyhexenoic acids to γ-vinyl-γ-butyrolactone, and that such conversion can occur upon heating the acetoxyhexenoic acids and monovalent copper in the presence of manganese and other components of a reaction mixture containing acetoxyhexenoic acids. However, the copper must be monovalent to be effective. Since monovalent copper cannot exist to a significant extent in the presence of trivalent manganese, it is necessary that manganese present be in the divalent or lower valence state. Of course, nominal amounts of trivalent manganese can be tolerated, if insufficient to oxidize substantially all of the cuprous ion present. Thus, the present invention involves the use of cuprous ion and heat to convert acetoxyhexenoic acids to γ-vinyl-γ-butyrolactone, and particularly such use in the presence of manganese.

The present invention is mainly concerned with conversion of acetoxyhexenoic acids to lactones, as the acetoxy acids are the ones ordinarily produced in the referred-to process. However, other acyloxyhexenoic acids can be used and converted to γ-vinyl-γ-butyrolactones in the same way, particularly those in which the acyloxy moiety is from an alkanoic acid, for example a lower alkanoic acid of 2 to 6 carbon atoms. Such 6-acyloxy-4-hexenoic acids and 4-acyloxy-5-hexenoic acids can be formed, for example, by transesterification of the corresponding acetoxy acids with the appropriate alkanoic acid or acid chloride.

The present process can be effected by heating acetoxyhexenoic acids, preferably in a solvent, with cuprous ion. The cuprous ion can be supplied in the form of cuprous acetate, cuprous chloride, cuprous oxide, etc. Also, copper can be provided in various forms and converted in situ to the cuprous form. Thus, various cupric salts can be reduced to cuprous salts. For example, a solution of cupric acetate containing acetoxyhexenoic acids can be subject to reduction at the cathode of an electrolysis cell, or be contacted with hydrogen gas, to convert the cupric acetate to cuprous acetate, and heating will then readily convert the acetoxyhexenoic acids to γ-vinyl-γ-butyrolactone. A wide range of temperatures will be operable for the conversion, such as from about 60° C. to about 200° C., but to obtain desirable reaction rates without unnecessarily high temperatures, it may be advantageous to use temperatures in the range of about 100° C. to about 180° C. or so. The amount of cuprous ion used can vary widely, but will often be in the range of about 2% to about 40% by weight of the acetoxyhexenoic acids. Similar amounts of platinum can be used, and ordinarily in zero valent state. In the event the acetoxyhexenoic acids are produced in a process using manganese and copper ions, it will generally be appropriate to use the copper in the quantity present in the reaction mixture, using means to reduce it to the cuprous state if necessary. Reaction mixtures from acetoxyacid processes involving use and regeneration of trivalent manganese will have appreciable concentrations of trivalent manganese at some stages of a continuous process; however, the trivalent manganese can be permitted to react till it is extensively utilized, and can be permitted to react further in a sidestream taken off for conversion of acetoxyhexenoic acids therein to lactone. Thus a sidestream can be heated to cause reaction of the trivalent manganese with acetic acid, acetic anhydride or other components of the reaction mixture with reduction to divalent manganese. The copper present may also be reduced to some extent to monovalent copper. The presence of monovalent copper can even be assured by subjecting the sidestream to reduction at the cathode of an electrolysis cell, or by contacting the sidestream with hydrogen gas. This will also serve to reduce residual trivalent manganese if any is still present.

The present process in a particular embodiment involves heating the acetoxyhexenoic acids in the presence of cuprous ion. The process can be carried out either with or without a solvent, although the acetoxyhexenoic acids as prepared will generally be in a solvent or liquid medium, and the conversion to lactone will generally be effected in such solvent or medium. If desired, of course, one or more components of the medium can be separated prior to conversion of acetoxyhexenoic acids to γ-vinyl-γ-butyrolactone. When acetoxyhexenoic acids are produced in solution in a medium such as acetic acid, the concentration of acetoxyhexenoic acids is preferably kept to values less than 10% by weight, so the present process may often be used with concentrations of acetoxyhexenoic acids less than 10% by weight.

Referring to FIG. 1, a flow sheet for preparation of acetoxyhexenoic acids and conversion to lactone, butadiene from line 1 and solvent electrolyte and other components from line 2 are added to recycle line 3 and enter reactor 4 for reaction at elevated temperature. The discharge from 4 comprising some acetoxyhexenoic acids, reactants, and substantial concentrations of manganous ions is oxidized to manganic ion. The discharge from the electrolysis cell flows through line 3 to reactor 4. A sidestream is taken off through line 7 which can go to a holding and heating vessel 8 for further reaction in order to reduce any remaining trivalent manganese to divalent manganese. The mixture then flows by line 9 through the cathode chamber of electrolysis cell 10 to reduce cupric ion to cuprous ion, and then by line 11 to reactor 12 for heating to convert the acetoxyhexenoic acids to γ-vinyl-γ-butyrolactone. From reaction 12 it proceeds by line 13 to line 5 to the electrolysis cell 6.

For product separation, part of the reaction stream can be permitted to flow through line 14 to separation zone 15. There, the acetoxyhexenoic acids and γ-vinyl-γ-butyryolactone can be separated from the other components, and discharged through line 16, while other components are returned to the reaction system through line 17. Various means of separation, employing extraction, distillation, etc. can be employed in the separation zone, which may result in separate product, solvent-reactant, and salt streams, and the solvent-reactant and salt streams can be separately recycled, or combined and recycled to the reaction.

In operation, the materials will react in reactor 4, producing substantial amounts of acetoxyhexenoic acids and resulting in reduction of substantial amounts of the metal oxidants to divalent manganese and possibly some monovalent copper. The reaction mixture is then cycled through electrolysis cell 6 in order to regenerate trivalent manganese for further use. The electrolysis cell will ordinarily involve two parallel planar electrodes separated by a relatively narrow gap, and employed with a fairly rapid flow of electrolyte between the electrodes. The cell can be either divided or undivided, but it may be convenient to use a cell with an ion exchange membrane divider and to circulate the electrolyte through the anode chamber. An example of appropriate membrane is Nafion ® 425 sulfonated polyether polymer. The process can be operated fairly effectively with from about 1% up to 4 or 5% or so acetoxyhexenoic acids present in the reaction mixture, so the side stream taken off by line 7 will be in sufficient volume that the concentrations of acetoxyhexenoic acids can be kept in such ranges. The space velocity and other factors in the side stream will generally be such that good conversion of the acetoxyhexenoic acids to lactone is obtained. The ratio of lactone to acetoxyhexenoic acids will often be about 9 to 1 in the stream returning to the reaction by line 13, and a fairly high ratio, possibly approaching 9:1, will often be maintained in the rest of the reaction system in continuous processes at steady state conditions.

It is known that acid catalysis at elevated temperature can convert γ-vinyl-γ-butyrolactone to sorbic acid. Ordinarily, the present process will be practised for the purpose of obtaining γ-vinyl-γ-butyrolactone as an intermediate to sorbic acid. However, it is not ordinarily a purpose of the present invention to convert the lactone to sorbic acid, particularly when the lactone is present in a reaction mixture with manganese ions and other components of an acetoxyhexenoic acid preparation process, as sorbic acid would undergo reactions and degrade in the presence of manganese salts and other components of an acetoxyhexenoic acid preparation process. It happens that in the absence of fairly strong acid, the lactone product has good stability in the reaction mixture and can be isolated therefrom.

In processes for producing acetoxyhexenoic acids from butadiene and acetic acid, it has been found that selectivity is initially fairly good, even in continuous processes with electrolytic regeneration of trivalent manganese ion. However, as the product builds up over certain levels, due to conversions, concentrations, or the concentrations used, the selectivity falls off; in particular, fairly good selectivity can be obtained with product concentrations of say 5 up to 7 or 8% by weight in a continuous procedure, but when this is exceeded or attempts are made to exceed a payload of 10% by weight, the selectivity to acetoxyhexenoic adids is markedly lower. Batch processes can be run to have somewhat higher final product concentrations, since part of the process is effected at very low product concentrations. Conducting the process at low product concentrations adds to the expense of the process, as it involves the use of more dilute solutions with larger volumes to handle, and a more frequent product separation or larger product stream for separation. A larger volume of materials for separation, by distillation or similar procedures adds to the cost of the procedure. It is apparent therefore that it will be advantageous to be able to run the preparative process to higher product concentrations.

The present invention can be effected in processes with usual concentrations of materials for the acetoxyhexenoic acid preparation, for example, with acetic acid and acetic anhydride as a solvent system with a range of about 0.2 to about 0.8 mole acetic anhydride per mole acetic acid, manganese ion in the range of about 10 to 300 millimoles per liter, with electrolytic regeneration to provide about 10 to about 50 millimoles of the manganese in the trivalent state, butadiene in the range of about 0.05 to 0.3 moles per liter, and copper in about 5 to 150 millimoles.

The process might be conducted in a temperature range of about 80° to about 120° C. Additional reactants can be added to maintain such concentrations, and the product take-off stream can be adjusted to have a desired product concentration in the reaction mixture. In carrying out the present invention it will be desirable to limit the amount of acetoxyhexenoic acids product in the reaction mixture, preferably to amounts no greater than 5% by weight. Thus the process can be run under conditions to have a steady product concentration less than 10% by weight, with provisions for a product ratio of 9 parts γ-vinyl-γ-butyrolactone to 1 part acetoxyhexenoic acids.

The present invention involves the conversion of acyloxyhexenoic acids to γ-vinyl-γbutyrolactone, and particularly such conversion in the presence of reactants and other components of the reaction mixture in which the acyloxyhexenoic acids were produced. While various means can be used, any method effective for the conversion is suitable. Heating to elevated temperatures is a simple method of effecting the conversion. While this method is usually relatively slow, it may be useful under some circumstances. Temperatures in the range of 100° to 180° C. or so can be used, and it may at times be desirable to use even higher temperatures. The use of high temperatures may be more effective in some cases than others, for example, depending upon the presence and concentration of other components of a reaction mixture containing acetoxyhexenoic acids.

EXAMPLE 1

A solution was prepared with components typical for an acetoxyhexenoic acid preparation reaction mixture, but with the copper therein in the divalent state. The solution contained acetic acid, 75 ml; acetic anhydride, 25 ml; $Mn(OAc)_2 \cdot 4H_2O$, 2 grams; $Cu(OAc)_2 H_2O$, 0.2 gram; KOAc, 5 grams; and 5 grams of a mixture of 6-acetoxy-4-hexenoic acid and 4-acetoxy-5-hexenoic acid. The solution was boiled under reflux at 120° C. nitrogen blanketed for 6 hours. Analysis by gas chromatography, benzophenone internal standard, showed a 16.8% conversion of acetoxyhexenoic acids with 16% selectivity to $\gamma$-vinyl-$\gamma$-butyrolactone. The slow conversion at the temperature employed indicates little or no catalytic activity of the divalent copper and divalent manganese.

The procedure of Example 1 was repeated, but with addition of 0.3 gram copper powder. In three hours, an 82% conversion was obtained, with 94% selectivity to $\gamma$-vinyl-$\gamma$-butyrolactone. The monovalent copper, produced by reaction of the copper powder and cupric acetate, served as an effective catalyst for the reaction.

EXAMPLE 3

The procedure of Example 1 was repeated but with addition of 0.3 gram platinum black. In 1.5 hours, a 16% conversion was obtained with 39% selectivity to $\gamma$-vinyl-$\gamma$-butyrolactone. It can be seen that the platinum increased the conversion rate markedly over that of Example 1.

EXAMPLE 4

A sample of reaction mixture which had been subjected to elevated temperature reaction conditions and to electrolysis at the anode to oxidize manganese and copper ions was utilized. The solution which was similar to that of Example 1, was heated under reflux, nitrogen blanketed at 120° C. for 6.5 hours. Analysis showed 81% conversion of the acetoxyhexenoic acids, with 94% selectivity to $\gamma$-vinyl-$\gamma$-butyrolactone. It is evident that some monovalent copper was present from the acetoxyhexenoic acid synthesis and catalyzed the reaction.

EXAMPLE 5

The procedure of Example 4 was repeated, but air was bubbled through the reaction mixture for one hour before heating it to reflux. The conversion was 21% after 6 hours and selectivity was 42% to $\gamma$-vinyl-$\gamma$-butyrolactone. The oxidation of the cuprous ion destroyed its activity.

EXAMPLE 6

The procedure of Example 4 was repeated but with addition of 0.3 gram copper powder. The conversion was 86%, with 96% selectivity to $\gamma$-vinyl-$\gamma$-butyrolactone.

EXAMPLE 7

A solution was formed from $Mn(OAc)_2$, 5 grams; KOAc, 10 grams; $Cu(OAc)_2$, 1 gram; acetoxyhexenoic acids, 8.7 grams; acetic acid, 75 ml; and acetic anhydride, 25 ml. The solution was placed in a pressure bottle and heated to 150° C., with magnetic stirring. After four hours, 4.91 gram of lactone had formed, and 1.25 grams acetoxyhexenoic acids was recovered for 88% conversion and 100% selectivity. Lactone formation in the unelectrolyzed solution was fairly slow even at 150° C.

EXAMPLE 8

The solution and procedure of Example 7 were used, but with addition of 50 mg. copper powder. After only 1.5 hours, a 70% conversion was obtained with 80% selectivity to $\gamma$-vinyl-$\gamma$-butyrolactone. The amount of product was approximately the same as obtained in Example 7 after 3 hours.

EXAMPLE 9

The solution and procedure of Example 7 were used, but with addition of 0.5 gram copper metal powder. At 20 minutes, 93% conversion was obtained with 100% selectivity to $\gamma$-vinyl-$\gamma$-butyrolactone.

EXAMPLE 10

A solution was employed like that of Example 7, except that the amount of KOAc was 10 grams, and the amount of acetoxyhexenoic aciecs was 10 grams. The solution was placed in a glass pressure bottle and hydrogen was bubbled through it at atmospheric pressure for 5 minutes. The bottle was then sealed and heated to 150° C., causing a rise in pressure to 42 psi gauge. After 1 hour the conversion was 88% and selectivity to $\gamma$-vinyl-$\gamma$-butyrolactone was 84%. The reduction of cupric acetate to the cuprous form made it an active catalyst.

EXAMPLE 11

A solution like that of Example 7 was employed, except that the amount of acetoxyhexenoic acids was 7.8 gram. The solution, in a pressure bottle, was electrolyzed in contact with a graphite felt cathode. The solution was separated from the platinum wire anode by an Alundum cup. Electrolysis was carried out at 0.2 ampere for 28 minutes. The pressure bottle was then heated at 150° C. for 30 minutes. Conversion was 85.1% with 80% selectivity to $\gamma$vinyl-$\gamma$-butyrolactone. It is evident that copper was reduced to the cuprous form at the cathode to form an effective catalyst.

EXAMPLE 12

The following illustrates the relationship of acetoxyhexenoic acid concentration to cumulative current efficiency, using a divided electrochemical cell operating as a batch process.

Figure 2:
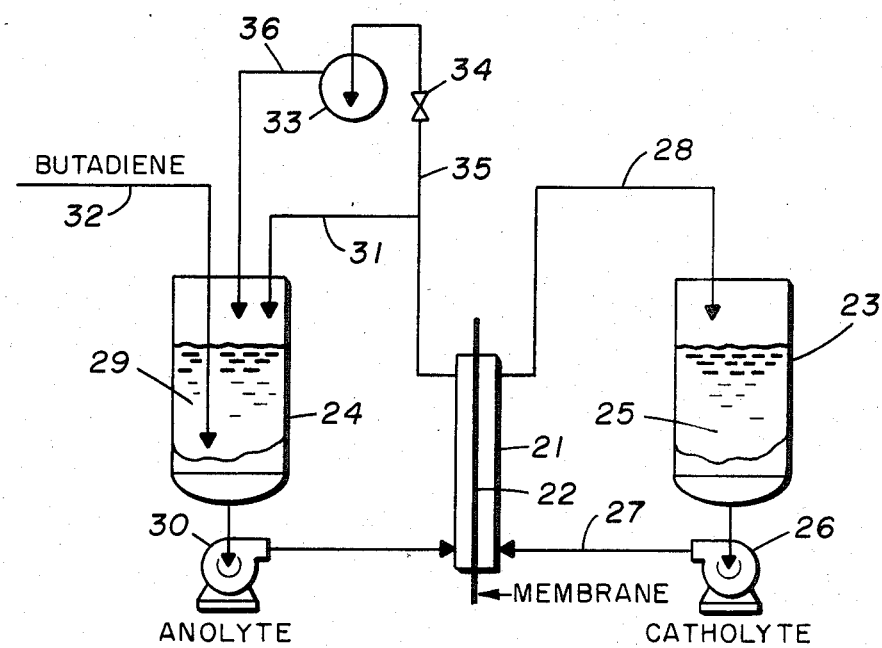

The system is depicted schematically in FIG. 2. The system has a divided electrolysis cell 21 with membrane divider 22, and catholyte reservoir 23 and anolyte reservoir 24. The catholyte 25 is circulated from catholyte reservoir 23 by pump 26 through line 27 to the catholyte side of the electrolysis cell 21 and back through line 28 to the catholyte reservoir. The anolyte 29 in reservoir 24 is circulated by pump 30 through the anolyte side of cell 21 and through line 31 back to the anolyte reservoir. Butadiene is sparged into the anolyte by line 32. The anolyte system is also provided with a smaller reservoir 33 and a portion of the anolyte can, if desired, be shunted to that reservoir through valve 34 via line 35, and then returned to the anolyte reservoir by line 36.

The plate and frame divided electrochemical cell 22 was constructed of stainless steel back-plates with Teflon ® gaskets used to form the anolyte and catholyte passages. Anode and cathode surfaces were 3 cm×15 cm with inlets at each end of the longer dimension. Inlet and exit were tapered to aid streamlined flow. The anolyte and catholyte compartments were separated by a member 22 of Nafion ® 425 sulfonated polyether polymer. Spaces provided ⅛" (0.16 cm) of gap between the membrane and each electrode such that the overall cell gap was ¼" (0.32 cm). Within each compartment was a mesh of polypropylene with approximately ∼¼" (0.32 cm) square grids and having a thickness of ∼⅛" (0.16 cm) (CONWED XN5010). The mesh rested against the electrodes, masking each such that the effective area of each electrode was about 28 cm². Gaseous 1,3-butadiene was sparged into the anolyte continuously, maintaining a saturated solution of the diene.

In the cell, an anode of Union Carbide WDF graphite felt (∼¼" (0.32 cm) thick) and a cathode of stainless steel were used.

An anolyte solution consisting of:

| | |
|---|---|
| Manganese (II) acetate tetrahydrate | 25 g. |
| Copper (II) acetate monohydrate | 1 g. |
| Sodium acetate | 62.5 g. |
| Acetic acid | 295 ml. |
| Acetic anhydride | 145 ml. | and a catholyte consisting of:

| | |
|---|---|
| Sodium acetate | 100 g. |
| Acetic acid | 880 ml. |
| Acetic anhydride | 35 ml. | were charged to their respective reservoirs. The solutions were maintained at about 100° C. and were circulated through the cell at a rate of about 3 liters/min.

Figure 3:
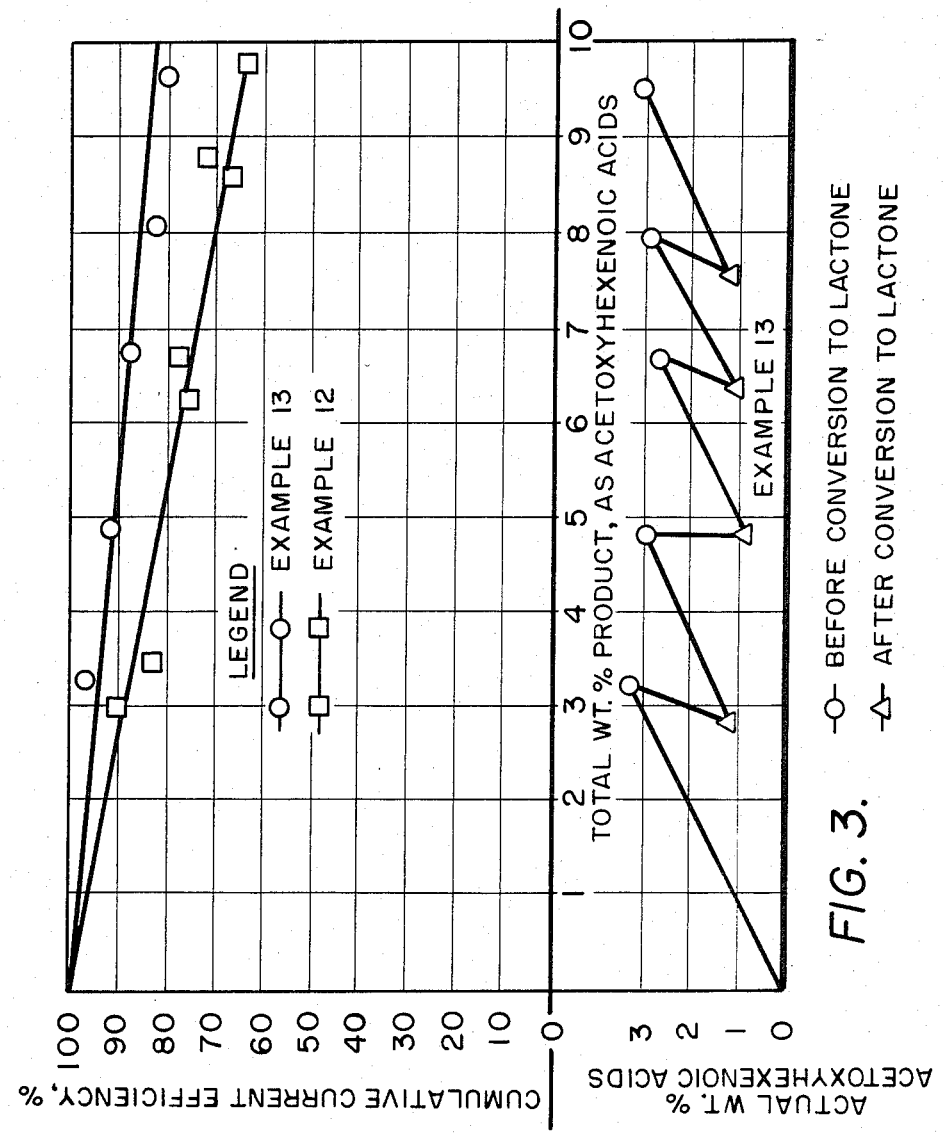

The system was electrolyzed at a constant current of 3.5 amps for 6.75 hrs. during which time 110 g. of sodium acetate was added to the anolyte. Samples of anolyte were periodically withdrawn and analyzed for acetoxyhexenoic acids via vapor phase chromatography (VPC). This data is graphically reported in FIG. 3 (as one of the Graphs) in terms of cumulative current efficiency to acetoxyhexenoic acids vs. the cumulative weight percent of acetoxyacids produced, (as a percent of the reaction mixture) and in this example, actually present in the reaction mixture. It will be noted that the current efficiency over the course of the reaction declined from about 100% to about 65%.

Essentially the same results were obtained with potassium acetate and lithium acetate in place of sodium acetate as the supporting electrolyte and with higher or lower applied current. Additionally, variation in copper (II) acetate from 5-100 mmol/liter were found to produce essentially no change in results.

EXAMPLE 13

The electrochemical cell system described in Example 12 and illustrated in FIG. 2 was fitted with a WDF graphite felt cathode (Union Carbide). In addition, for a particular stage of the procedure it was planned to shunt a portion of the anolyte stream through a 250 ml. reservoir 33 where the portion is heated to approximately 135° C. before returning to the main reservoir.

An anolyte solution consisting of:

| | |
|---|---|
| Manganese (II) acetate tetrahydrate | 25 g. |
| Copper (II) acetate monohydrate | 7.3 g. |
| Potassium acetate | 75 g. |
| Acetic acid | 305 ml. |
| Acetic anhydride | 145 ml. | and a catholyte solution consisting of:

| | |
|---|---|
| Potassium acetate | 60 g. |
| Acetic acid | 440 ml. |
| Acetic anhydride | 15 ml. | were charged to their respective reservoirs. The solutions were maintained at about 100° C. and were circulated through the cell at a rate of about 3 liters/minute. The anolyte was saturated with 1,3-butadiene by continuous sparging.

The system was electrolyzed for a period of 2-3 hours at a constant current of 3 amperes after which the current was turned off. After the characteristic Mn(III) acetate color disappeared from the anolyte, the shunt valve 34 was opened to allow about 0.5 l/min of anolyte to flow through the shunt system. The temperature of the small reservoir in the shunt system was maintained at about 135° C. The polarity of the cell was then reversed such, that the electrode that was normally an anode was made cathodic. The system was electrolyzed in this manner for 0.5 hr. at 1 amp to deposit metallic copper (O) in the product solution. The current was then turned off and the solution was allowed to circulate for ∼1 hr. after which time VPC analysis of the anolyte showed approximately two-thirds of the acetoxyhexenoic acids originally contained therein had been converted to γ-vinyl-γ-butyrolactone. This process was then repeated several times until a total product payload of 9.5 wt % of the reaction mixture (calculated as acetoxyhexenoic acid) was obtained. A total of 75 g. of potassium acetate was added to the anolyte during the electrolysis. The results are presented graphically in FIG. 3 in comparison to those of Example 12. It can be seen that the results in the present Example 13 with a final current efficiency around 80% are markedly improved over those of Example 12. The current efficiency in Example 13 takes into account both the acetoxyhexenoic acid and γ-vinyl-γ-butyrolactone products. On the lower part of FIG. 3 the actual weight percentages of acetoxyhexenoic acids present in the reaction mixture at particular times in Example 13 are plotted vs. the cumulative percent of acetoxyhexenoic acids produced (as a percent of the reaction mixture). It can been seen that the intermittent conversion to lactone permitted a cumulative acetoxyhexenoic acids production of 9.5% by weight of the reaction mixture, although the actual concentration of such acids was kept to about 3% or lower.

Figure 4:
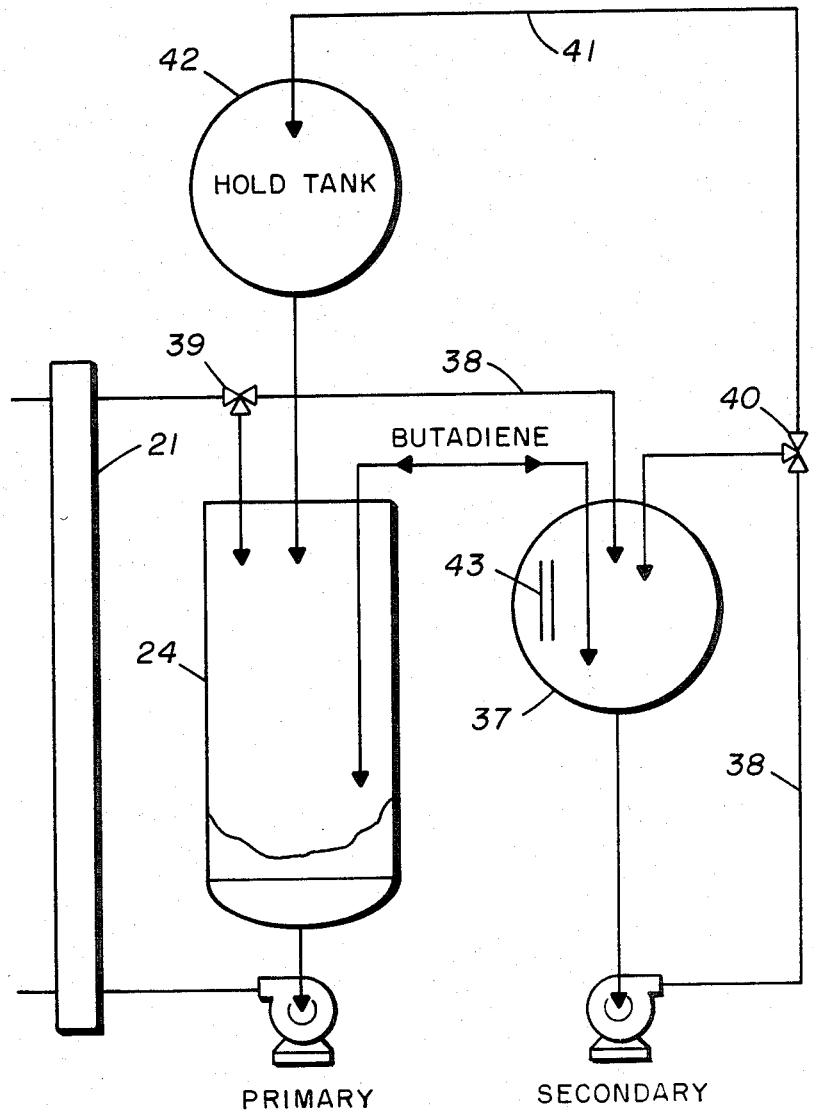

FIG. 4 illustrates a modification of the anolyte portion of the system of FIG. 2 in which the electrolysis cell 21 and, primary anolyte reservoir 24, are essentially as in FIG. 2, although the effective area of the anode in the cell has been increased to 65 cm². The system is fitted with a secondary reservoir 37 and line 38 and valve 39 so that the discharge from electrolysis cell 21 can be conducted to either primary resevoir 24 or secondary reservoir 37. Also valve 40 permits circulation of anolyte from reservoir 37 to recycle to the reservoir, or via line 41 to holding reservoir 42, from which it can be discharged to primary reservoir 24. The secondary reservoir 37 is equipped with electrodes 43, connected to positive and negative current sources for electrolysis. The electrodes of Union Carbide WDF graphite felt had a geometrical area of about 28 cm$^2$ each and the gap between the electrodes was about 7 mm.

EXAMPLE 14

The equipment illustrated in FIG. 4 was employed for an electrolysis. The system had primary and secondary anolyte reservoirs and separate ciruculation pumping loops, with a hold tank and means for transfer between the reservoirs. Thus the system allowed production of acetoxyhexenoic acids in the primary system, followed by conversion to γ-vinyl-γ-butyrolactone in the secondary system. By utilizing two anolye reservoirs the processes can be carried out simultaneously.

An anolyte solution consisting of:

| | |
|---|---|
| Manganese (II) acetate, tetrahydrate | 150 g. |
| Copper (II) acetate monohydrate | 43 g. |
| Potassium acetate | 428 g. |
| Lithium acetate dihydrate | 54 g. |
| Acetic Acid | 1400 ml. |
| Acetic Anhydride | 1050 ml. | and a catholyte solution consisting of:

| | |
|---|---|
| Potassium Acetate | 300 g. |
| Acetic Acid | 2410 ml. |
| Acetic Anhydride | 90 ml. | were charged to their respective reservoirs and maintained at about 100° C. The anolyte was kept saturated with 1,3-butadiene.

Figure 5:
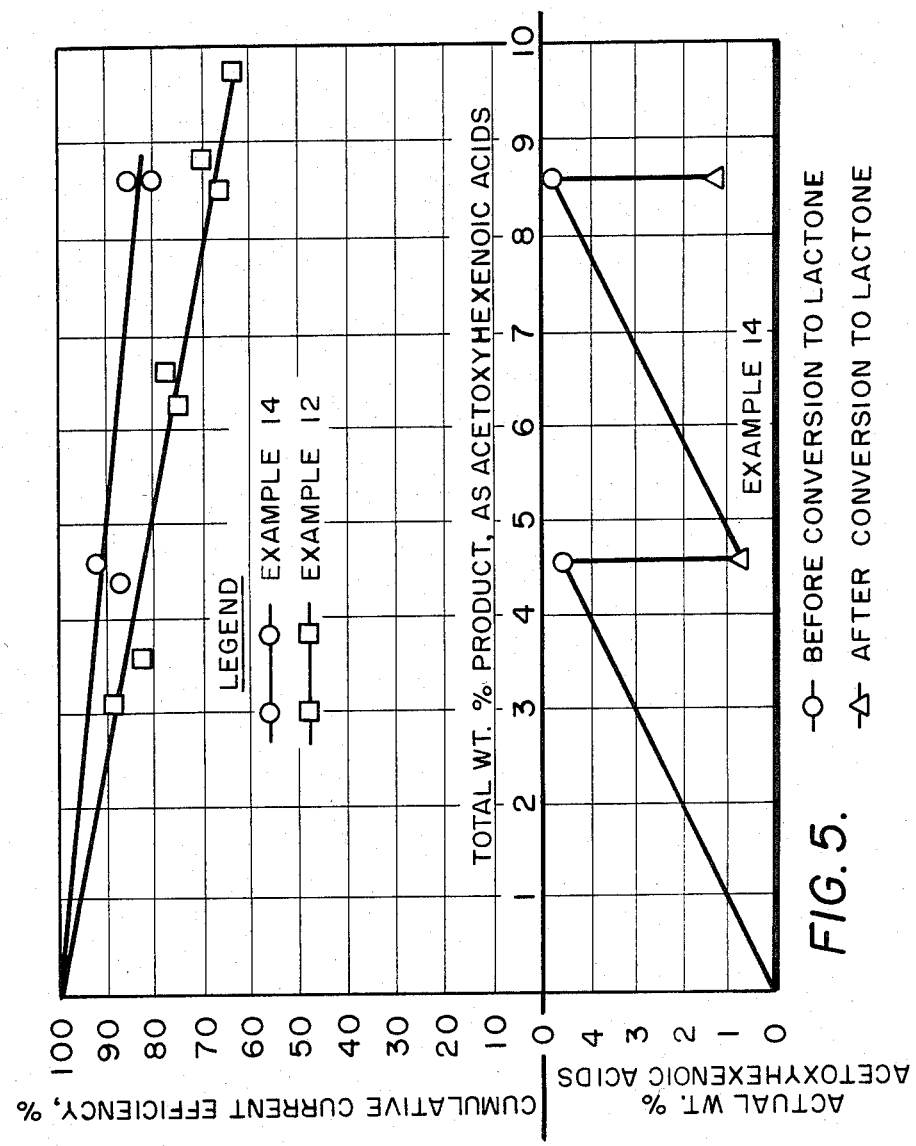

The system was electrolyzed for 10 hr at 5 amps current after which time 200 g of potassium acetate was added and the anolyte was transferred to the secondary reservoir. A new charge of the same anolyte solution was charged to the primary reservoir and electrolyzed as above with addition of butadiene. Concurrently, the anolyte solution in the secondary reservoir was subjected to 1 hr of electrolysis at 1.5 amps at 100°–130° C., held for 3 hr at reflux (130°–135° C.) to convert the acetoxyacids product to lactone, then allowed to cool to 100° C. The original anolyte was then returned to the primary reservoir via the hold tank while the contents of the primary reservoir were transferred to the secondary reservoir. The process was thus repeated until each batch of anolyte had experienced in order 2 cycles of 50 Amp hr. Electrolysis in the primary reservoir followed by the above described 1.5 amp. hr electrolysis and reflux treatment in the secondary reservoir. In FIG. 5 the results are compared graphically to Example 12. It can be seen that current efficiency in the Example 14 procedure was better than 80% after production of approximately 8.5% by weight acetoxyhexenoic acids. On the lower part of FIG. 5, the actual concentrations of acetoxyhexenoic acids concentration was kept at levels below 5% by weight.

EXAMPLE 15

A Pope Scientific jacketed 2 inch diameter wiped film molecular still was modified and attached at its lower outlet to a separation distillation column below the midpoint of the column. The wiped surfaces were maintained at approximately 155°–160° C. by circulating heated oil through the jacket. The vapor outlet from the still was heated to prevent condensation before entering the column. The column was 2.5 cm internal diameter by 80 cm long and was packed with 3/16" glass helices. A 3 cm length of the bottom of the column was maintained at 135°–140° C. to serve as a reboiler. The center 55 cm of length of column was maintained at about 100° C. by circulation of heated fluid through a jacket surrounding this section. No heat was applied to the top 22 cm length of the column. Vapor exiting the top of the column was condensed at about 20° C. The entire system was maintained at about 80 mm Hg pressure via a vacuum pump.

A 2024 g. portion of product anolyte solution from Example 14 containing 92.8 g. of γ-vinyl-γ-butyrolactone was fed over about 4.6 hr into the top of the wiped film still. The residual salt heel remained fluid and was collected separately from an outlet at the bottom of the wiped film still after flowing down the walls of the still. 102.5 grams of liquid was collected from the bottom of the distillation column and analysis showed it contained 75.2 g of γ-vinyl-γ-butyrolactone.

About 1450 g of liquid was collected from the top of the column and analysis showed it to contain 7.4 g of γ-vinyl-γ-butyrolactone. The results demonstrate that γ-vinyl-γ-butyrolactone is readily separable from the reaction mixture by distillation.

EXAMPLE 16

Example 15 was repeated except that the feed solution consisted of:

| | |
|---|---|
| Manganese (II) acetate tetrahydrate | 15 g. |
| Copper (II) acetate monohydrate | 4.2 g. |
| Potassium acetate | 31.5 g. |
| Lithium acetate dihydrate | 6.3 g. |
| Acetic acid | 165 ml |
| Acetic anhydride | 105 ml |
| γ-vinyl-γ-butyrolactone | 26.8 g. |
| Acetoxyhexenoic acids | 5.0 g. | and was fed over about 0.8 hr. Analytical results are as follows:

Still bottom liquid: 28.5 g. total wt. 24.2 g. γ-vinyl-γ-butyrolactone.

Still top condensate: 272 g. total wt. Contains no γ-vinyl-γ-butyrolactone.

Salt heel contains: 3.8 g. γ-vinyl-γ-butyrolactone; 2.7 g. Acetoxyhexenoic acids.

Procedures for distilling γ-vinyl-γ-butyrolactone from a molten salt and recycling the salt are further described in a commonly assigned U.S. patent application of two of us, simultaneously filed herewith. Ser. No. 503,982, filed June 6, 1983.

We claim:

1. A process for preparing γ-vinyl-γ-butyrolactone in which butadiene and acetic acid are reacted in the presence of metal ion oxidants to produce acetoxyhexenoic acids, and the reaction mixture in a subsequent stage is treated to convert acetoxyhexenoic acids to γ-vinyl-γ-butyrolactone, and in which γ-vinyl-γ-butyrolactone-containing reaction mixture is recycled to the stage in the process producing acetoxyhexenoic acids.

2. The process of claim 1 in which manganese ion is employed.

3. The process of claim 1 in which cuprous ion or platinum is present during the subsequent stage.

4. The process of claim 1 in which the process is carried out on a continuous basis and the average acetoxyhexenoic acid concentration in the reaction mixture is less than about 5% by weight.

5. The process of claim 4 in which acetoxyhexenoic acids are converted to γ-vinyl-γ-butyrolactone by heating such acids in the presence of cuprous ion or platinum black.

6. The process of claim 5 in which manganese is also present.

7. The process of claim 5 in which acetoxyhexenoic acids are present in a reaction mixture resulting from reaction of butadiene, acetic acid, acetic anhydride and manganese and copper ions.

8. The process of claim 5 in which cuprous ion has been provided by reduction of cupric ion.

9. The process of claim 7 in which trivalent manganese was used as an oxidant but reaction of the components of the reaction mixture has been effected to an extent that substantially all of the manganese is in the divalent or lower valence state during the heating for conversion to lactone.

10. In a process for preparing sorbic acid precursors by reaction of butadiene and acetic acid with a manganese ion oxidant, the improvement which comprises carrying out the reaction in the presence of substantial amounts of acetic anhydride and obtaining good selectivity to acetoxyhexenoic acids, and in a subsequent stage converting the acetoxyhexenoic acids in the reaction mixture to γ-vinyl-γ-butyrolactone and recycling the γ-vinyl-γ-butyrolactone-containing reaction mixture to the stage in the process producing acetoxyhexenoic acids.

11. The process of claim 10 in which heating is employed in the conversion to lactone.

12. The process of claim 10 in which trivalent manganese is regenerated by electrolysis during preparation of acetoxyhexenoic acids.

13. The process of claim 10 in which the process is carried out on a continuous basis with recycling from the subsequent stage to the acetoxyhexenoic acid preparation stage and to have an average acetoxyhexenoic acid concentration in the reaction mixture less than about 5% by weight and a γ-vinyl-γ-butyrolactone concentration between about 5 and about 10% by weight.

14. A process for preparing γ-vinyl-γ-butyrolactone which comprises reacting butadiene, acetic acid and acetic anhydride with trivalent manganese as a metal ion oxidant to produce acetoxyhexenoic acids and heating such acetoxyhexenoic acid with cuprous ion to produce γ-vinyl-γ-butyrolactone and recycling the γ-vinyl-γ-butyrolactone-containing reaction mixture to the stage in the process producing acetoxyhexenoic acids.

15. The process of claim 14 in which the acetoxyhexenoic acids are heated to temperatures in the range of 100° to 180° C.

16. The process of claim 14 in which copper is also present with components reacting to produce acetoxyhexenoic acids, and is converted to the cuprous state for heating with the acetoxyhexenoic acids.

17. The process of claim 14 in which the amount of acetic anhydride is in the range of about 0.2 to about 0.8 mole per mole of acetic acid, manganese is in the range of about 10 to about 300 millimoles per liter, butadiene in the range of about 0.05 to about 0.3 mole per liter, and copper is present in the range of about 5 to 150 millimoles per liter.

* * * * *